United States Patent
An et al.

(10) Patent No.: US 11,156,482 B2
(45) Date of Patent: Oct. 26, 2021

(54) CONTACTLESS SENSOR MOUNTING SYSTEM FOR VEHICLE

(71) Applicants: Hyundai Motor Company, Seoul (KR); Kia Motors Corporation, Seoul (KR)

(72) Inventors: Dae Yun An, Gyeonggi-do (KR); Sang Kyung Seo, Seoul (KR); Gyun Ha Kim, Incheon (KR); Eung Hwan Kim, Seoul (KR); Yoon Seok Choi, Ulsan (KR)

(73) Assignees: Hyundai Motor Company, Seoul (KR); Kia Motors Corporation, Seoul (KR)

( * ) Notice: Subject to any disclaimer, the term of this patent is extended or adjusted under 35 U.S.C. 154(b) by 127 days.

(21) Appl. No.: 16/672,748

(22) Filed: Nov. 4, 2019

(65) Prior Publication Data

US 2021/0055137 A1    Feb. 25, 2021

(30) Foreign Application Priority Data

Aug. 20, 2019    (KR) ......................... 10-2019-0101842

(51) Int. Cl.
| | |
|---|---|
| *B60R 11/00* | (2006.01) |
| *G01D 11/10* | (2006.01) |
| *G01D 11/30* | (2006.01) |
| *A61B 5/00* | (2006.01) |
| *B60R 16/02* | (2006.01) |
| *G01S 7/28* | (2006.01) |

(52) U.S. Cl.
CPC ............ *G01D 11/10* (2013.01); *A61B 5/6893* (2013.01); *B60R 11/00* (2013.01); *B60R 16/02* (2013.01); *G01D 11/30* (2013.01); *G01S 7/28* (2013.01)

(58) Field of Classification Search
CPC ........ G01D 11/10; G01D 11/30; B60R 11/00; B60R 16/02
See application file for complete search history.

(56) References Cited

U.S. PATENT DOCUMENTS

| | | | |
|---|---|---|---|
| 10,239,432 B2* | 3/2019 | Subat | ..................... B60N 2/885 |
| 10,953,793 B2* | 3/2021 | Ali | ......................... B60R 16/02 |
| 2009/0152933 A1* | 6/2009 | Casey | ................. B60R 21/0155 |
| | | | 297/480 |
| 2015/0045984 A1* | 2/2015 | Hui | ...................... B60N 2/0248 |
| | | | 701/1 |

(Continued)

FOREIGN PATENT DOCUMENTS

| | | | |
|---|---|---|---|
| JP | 2008014871 A | * | 1/2008 |
| JP | 2019093974 A | * | 6/2019 |

*Primary Examiner* — Jamel E Williams
(74) *Attorney, Agent, or Firm* — Mintz Levin Cohn Ferris Glovsky and Popeo, P.C.; Peter F. Corless

(57) ABSTRACT

A contactless sensor mounting system for a vehicle is provided. The system includes a contactless sensor that is mounted in an interior component of the vehicle and having a first surface and a second surface opposing each other. A bracket is disposed around the contactless sensor and is fixed to the interior component. A first buffer member is interposed between the first surface of the contactless sensor and the interior component. A second buffer member is mounted on the second surface of the contactless sensor. Additionally, a leaf spring presses the second buffer member and the contactless sensor toward the interior component.

10 Claims, 19 Drawing Sheets

(56) References Cited

U.S. PATENT DOCUMENTS

2018/0178652 A1\* 6/2018 Monroe .................. B60Q 3/51
2019/0008050 A1\* 1/2019 Ali .......................... B60Q 3/80
2020/0116847 A1\* 4/2020 Jeon ....................... G01S 7/412

\* cited by examiner

CONTACTLESS SENSOR MOUNTING SYSTEM FOR VEHICLE

CROSS-REFERENCE TO RELATED APPLICATION

This application is based on and claims the benefit of priority to Korean Patent Application No. 10-2019-0101842, filed on Aug. 20, 2019, the disclosure of which is incorporated herein in its entirety by reference.

TECHNICAL FIELD

The present disclosure relates to a contactless sensor mounting system for a vehicle, and more particularly, to a contactless sensor mounting system for a vehicle that minimizes vibration transmitted to a contactless sensor mounted in an interior component of the vehicle such as a seat.

BACKGROUND

A vehicle is equipped with a variety of sensors. Some sensors may be mounted within interior components of the vehicle, such as a steering wheel, a cockpit module, and a seat, based on the purpose or use thereof. The sensors mounted within the interior components may be divided into a contact sensor and a contactless sensor using radio waves. Meanwhile, the contactless sensor using radio waves may receive vibration based on a mounting position, mounting structure, etc., which may reduce the sensing performance thereof.

Recently, a vehicle healthcare system has been developed to monitor the driver's biometric information, health conditions, and the like, thereby managing the driver's health or preventing traffic accidents. The vehicle healthcare system may have various healthcare sensors (e.g., a heart rate sensor or pulse sensor, an electrocardiogram (ECG) sensor, etc.) configured to measure the driver's heart (pulse) rate, ECG, and the like. The healthcare sensors may be mounted in the steering wheel, the cockpit module, the seat, and the like.

The healthcare sensors may be divided into a contact sensor and a contactless sensor. In particular, when vibration is transmitted to the contactless healthcare sensor based on the mounting position, mounting structure, etc., the sensing performance of the healthcare sensor may be degraded. For example, a radar pulse sensor, which is a contactless sensor, may be embedded within the vehicle seat and may be configured to measure the driver's heart (pulse) rate and the like using the Doppler radar principle. Since signals received by the radar pulse sensor include respiration, heart rate, and other noise components, accurate signal processing is required. However, when vibration is transmitted to the radar pulse sensor, the signals received by the radar pulse sensor may include external noise, which degrades the sensing performance of the radar pulse sensor.

The above information described in this background section is provided to assist in understanding the background of the inventive concept, and may include any technical concept which is not considered as the prior art that is already known to those skilled in the art.

SUMMARY

The present disclosure provides a contactless sensor mounting system for a vehicle, capable of minimizing vibration transmitted to a contactless sensor mounted within an interior component of the vehicle such as a seat.

According to an aspect of the present disclosure, a contactless sensor mounting system for a vehicle may include: a contactless sensor mounted within an interior component of the vehicle, and having a first surface and a second surface opposing each other; a bracket disposed around the contactless sensor, and fixed to the interior component; a first buffer member interposed between the first surface of the contactless sensor and the interior component; a second buffer member mounted on the second surface of the contactless sensor; and a leaf spring pressing the second buffer member and the contactless sensor toward the interior component.

The bracket may have a main opening in which the contactless sensor is received, and an exterior surface of the contactless sensor may be spaced apart from an edge of the main opening. The bracket may have a mounting lug which is coupled to the interior component. The interior component may have a first recess in which the first buffer member is received, and a second recess in which the mounting lug is received. The first buffer member may have a depression recess in which at least a portion of the contactless sensor is received. The second buffer member may include a base attached to the second surface of the contactless sensor, and a pair of legs that extend from both ends of the base toward the first buffer member, respectively.

The leaf spring may include a spring portion that supports the base, and a pair of resilient legs that extend from both ends of the spring portion toward the bracket. The leaf spring may have a pair of first snap fitting portions. The first snap fitting portions may be formed at ends of the resilient legs, respectively. The bracket may have a pair of second snap fitting portions, and the first snap fitting portions may be snap-fitted to the second snap fitting portions, respectively.

The contactless sensor may have a plurality of support lugs which are supported by portions of the interior component adjacent to a periphery of the first recess. A holding member for holding an electric wire that extends from the contactless sensor may be fixed to a top surface of the bracket. An electrical connector may be fixed to a top surface of the mounting lug.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Figure 1:
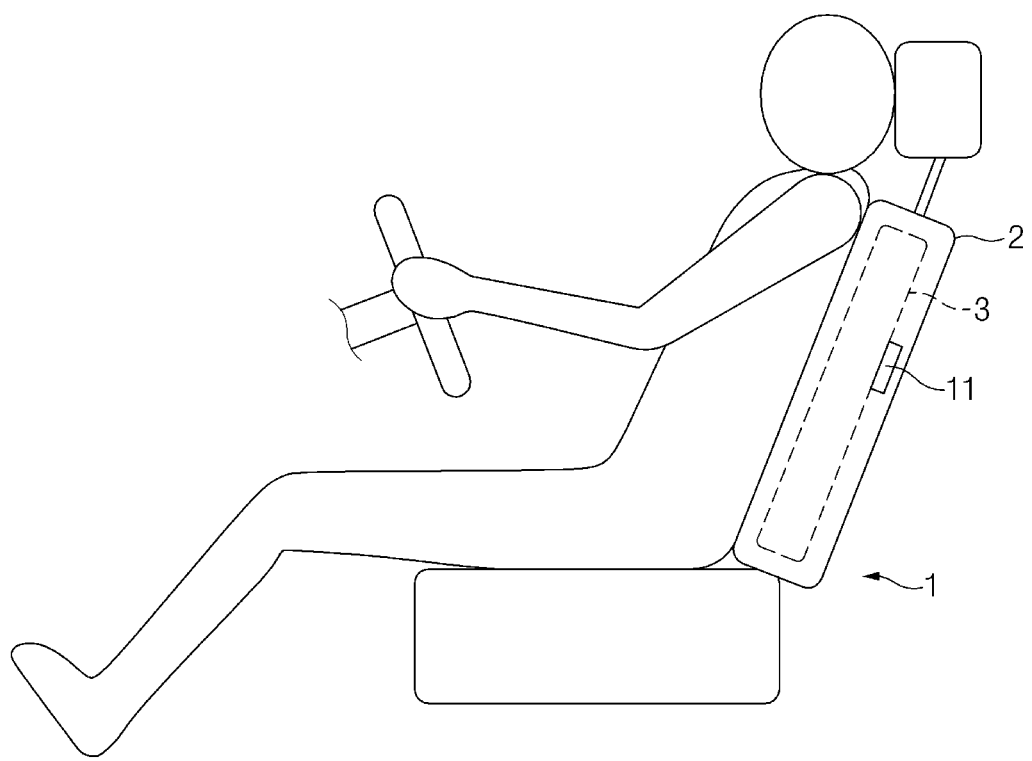
FIG. 1 illustrates a state in which a contactless sensor mounting system for a vehicle according to an exemplary embodiment of the present disclosure is disposed on a vehicle seat.

It is understood that the term "vehicle" or "vehicular" or other similar term as used herein is inclusive of motor vehicles in general such as passenger automobiles including sports utility vehicles (SUV), buses, trucks, various commercial vehicles, watercraft including a variety of boats and ships, aircraft, and the like, and includes hybrid vehicles, electric vehicles, combustion, plug-in hybrid electric vehicles, hydrogen-powered vehicles and other alternative fuel vehicles (e.g. fuels derived from resources other than petroleum).

Although exemplary embodiment is described as using a plurality of units to perform the exemplary process, it is understood that the exemplary processes may also be performed by one or plurality of modules. Additionally, it is understood that the term controller/control unit refers to a hardware device that includes a memory and a processor. The memory is configured to store the modules and the processor is specifically configured to execute said modules to perform one or more processes which are described further below.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items.

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Hereinafter, exemplary embodiments of the present disclosure will be described in detail with reference to the accompanying drawings. In the drawings, the same reference numerals will be used throughout to designate the same or equivalent elements. In addition, a detailed description of well-known techniques associated with the present disclosure will be ruled out in order not to unnecessarily obscure the gist of the present disclosure.

Terms such as first, second, A, B, (a), and (b) may be used to describe the elements in exemplary embodiments of the present disclosure. These terms are only used to distinguish one element from another element, and the intrinsic features, sequence or order, and the like of the corresponding elements are not limited by the terms. Unless otherwise defined, all terms used herein, including technical or scientific terms, have the same meanings as those generally understood by those with ordinary knowledge in the field of art to which the present disclosure belongs. Such terms as those defined in a generally used dictionary are to be interpreted as having meanings equal to the contextual meanings in the relevant field of art, and are not to be interpreted as having ideal or excessively formal meanings unless clearly defined as having such in the present application.

A contactless sensor mounting system for a vehicle, according to exemplary embodiments of the present disclosure, may be mounted in an interior component of the vehicle, and be configured to minimize vibration transmitted to a contactless sensor. In particular, the contactless sensor may be a sensor using radio waves.

According to an exemplary embodiment of the present disclosure, as illustrated in FIG. 1, the contactless sensor may be a radar pulse sensor 11 configured to sense a heart rate (pulse) of a driver using the Doppler radar principle, and the interior component of the vehicle may be a seatback 2 of a vehicle seat 1. The radar pulse sensor 11 may be embedded within the vehicle seat to sense the driver's heart rate and the like in a contactless manner. The radar pulse sensor may be configured to sense the driver's heart rate using the Doppler radar principle.

For example, the radar pulse sensor may have a transmitter configured to transmit radio waves toward a human body surface and a receiver configured to receive the radio waves reflected from the human body surface. A controller (not shown) may be configured to calculate the driver's heart rate by calculating a phase difference between transmitted and received signals. In particular, the radar pulse sensor 11 may be positioned adjacent to the driver's heart in the seatback 2, thereby more accurately sensing the driver's heart rate.

Figure 12:
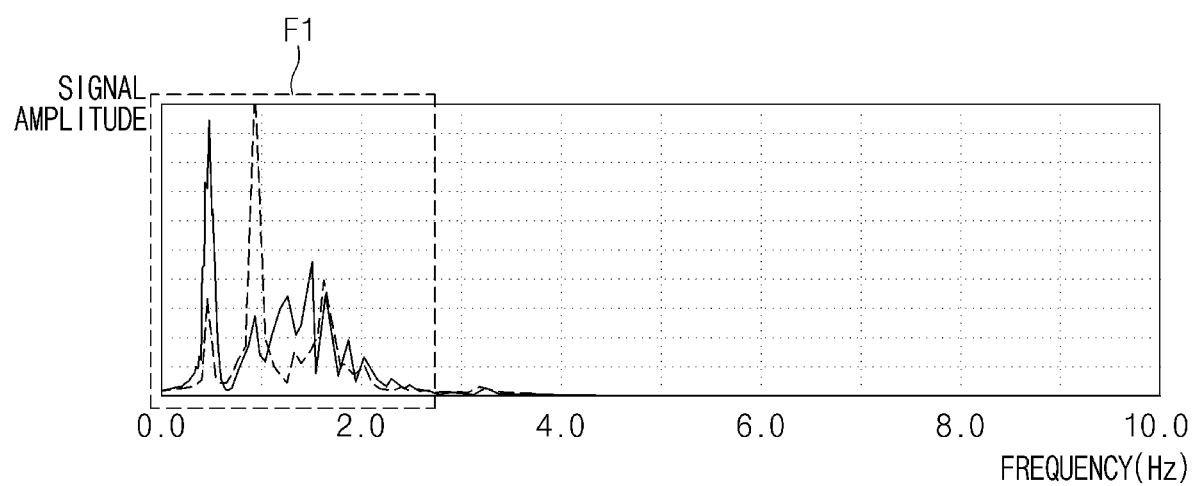
FIG. 12 illustrates a graph obtained by converting a signal output from an acceleration sensor mounted in a vehicle through fast Fourier transformation (FFT) analysis in a condition in which a radar pulse sensor senses a driver's heart (pulse) rate according to an exemplary embodiment of the present disclosure.
Figure 13:
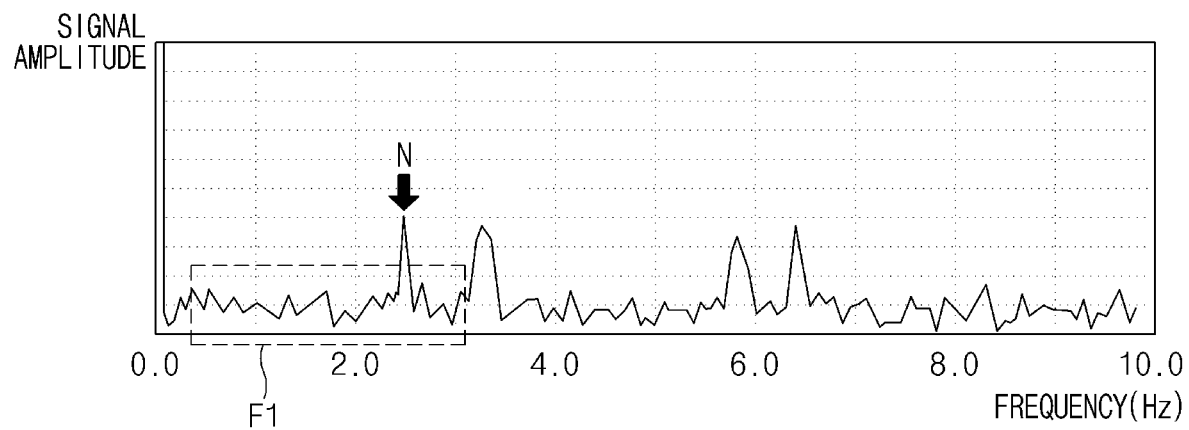
FIG. 13 illustrates a graph obtained by converting a signal output from an acceleration sensor mounted in a vehicle through FFT analysis in a condition in which a radar pulse sensor does not sense a driver's heart (pulse) rate according to an exemplary embodiment of the present disclosure.

FIGS. 12 and 13 illustrate graphs illustrating an algorithm for measuring the driver's heart rate by the radar pulse sensor 11. FIG. 12 illustrates a graph obtained by converting a signal output from an acceleration sensor mounted within the vehicle through fast Fourier transformation (FFT) analysis when the radar pulse sensor 11 senses the driver's heart rate. Referring to FIG. 12, the largest signal component may be extracted (selected) as the driver's heart rate at 0.8 Hz-3 Hz, which is a fundamental frequency band F1 of the heart rate. However, if external noise greater than the heart rate due to vibration is transmitted to the radar pulse sensor 11, the controller (not shown) may fail to accurately measure the driver's heart rate.

FIG. 13 illustrates a graph obtained by converting a signal output from the acceleration sensor mounted in the vehicle through FFT analysis in a condition in which the radar pulse sensor 11 does not sense the driver's heart rate. Referring to FIG. 13, when the vibration of the vehicle is transmitted to the radar pulse sensor 11 and the radar pulse sensor 11 does not sense the driver's heart rate, a noise signal N similar to the driver's heart rate is generated in the fundamental frequency band F1 of the heart rate. In other words, the radar pulse sensor 11 and the controller may misrecognize the noise caused by the vibration of the vehicle as the driver's heart rate.

When the radar pulse sensor 11 senses the driver's heart rate, the vibration of the vehicle may be transmitted to the radar pulse sensor 11 and thus, the controller may fail to accurately measure the driver's heart rate. Accordingly, the radar pulse sensor 11 may be provided to prevent the vibration of the vehicle from being transmitted to the radar pulse sensor 11. Specifically, the radar pulse sensor 11 may be mounted in a position to minimize the vibration of the vehicle transmitted to the radar pulse sensor 11. For example, when the radar pulse sensor 11 is mounted on a seat frame of the seatback 2, the vibration of the vehicle may be transmitted to the radar pulse sensor 11 through the seat frame of the seatback 2.

Figure 14:
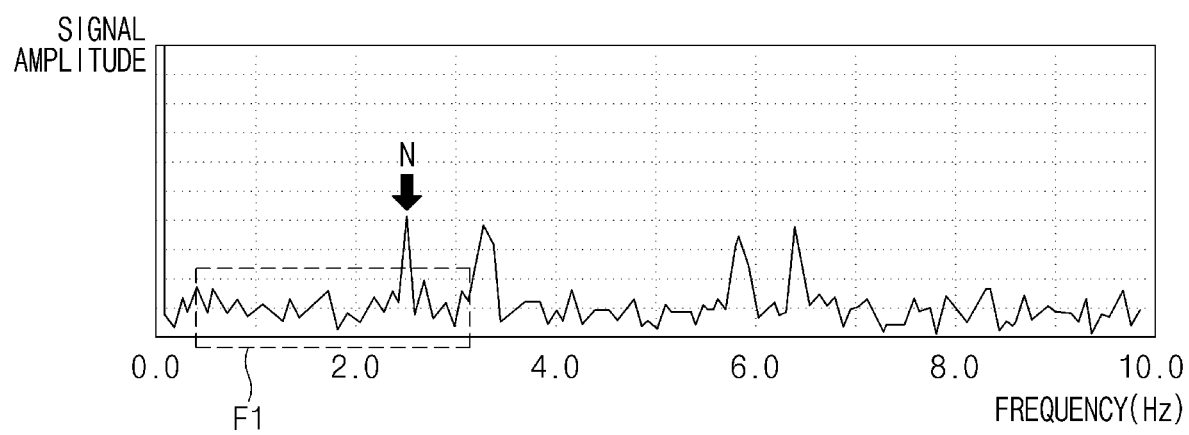
FIG. 14 illustrates a graph obtained by converting a signal output from an acceleration sensor mounted in a vehicle through FFT analysis in a condition in which a radar pulse sensor is mounted on a seat frame of a seatback according to an exemplary embodiment of the present disclosure.

FIG. 14 illustrates a graph obtained by converting a signal output from the acceleration sensor through FFT analysis in a condition in which the radar pulse sensor 11 is mounted on the seat frame of the seatback. Referring to FIG. 14, since the vibration of the vehicle is transmitted to the radar pulse sensor through the seat frame of the seatback 2, periodic noise N is generated in the fundamental frequency band F1 of the heart rate. In other words, when the radar pulse sensor is mounted on the seat frame of the seatback 2, it may be difficult to accurately measure the driver's heart rate due to the periodic noise N.

Figure 15:
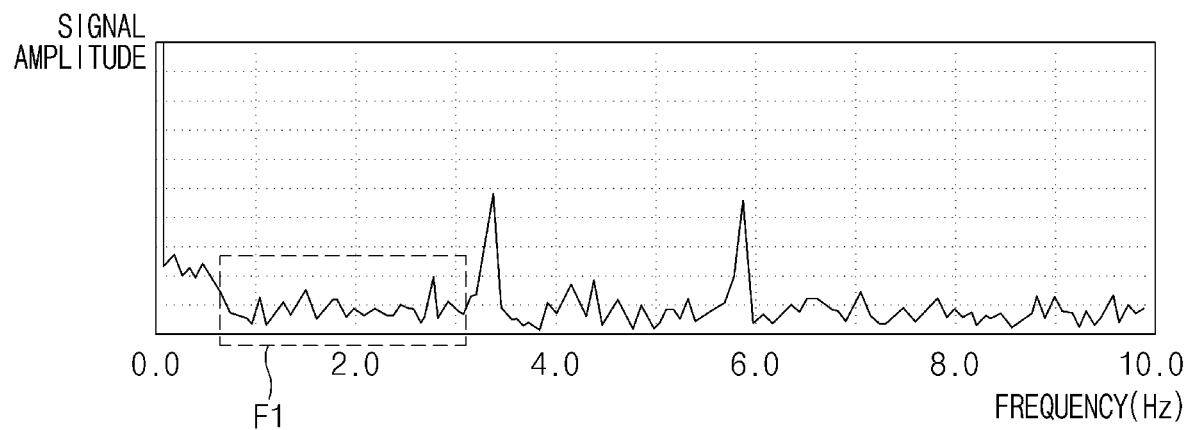
FIG. 15 illustrates a graph obtained by converting a signal output from an acceleration sensor mounted in a vehicle through FFT analysis in a condition in which a radar pulse sensor is mounted in a seatback foam pad of a seatback according to an exemplary embodiment of the present disclosure.

According to an exemplary embodiment of the present disclosure, the radar pulse sensor 11 may be mounted in a position where the transmission of vibration is minimized, such as a seatback foam pad 3, and thus, the transmission of vibration to the radar pulse sensor 11 may be minimized. FIG. 15 illustrates a graph obtained by converting a signal output from the acceleration sensor through FFT analysis in a condition in which the radar pulse sensor 11 is mounted in the seatback foam pad 3 of the seatback 2. Referring to FIG. 15, the periodic noise is hardly generated in the fundamental frequency band F1 of the heart rate.

Figure 2:
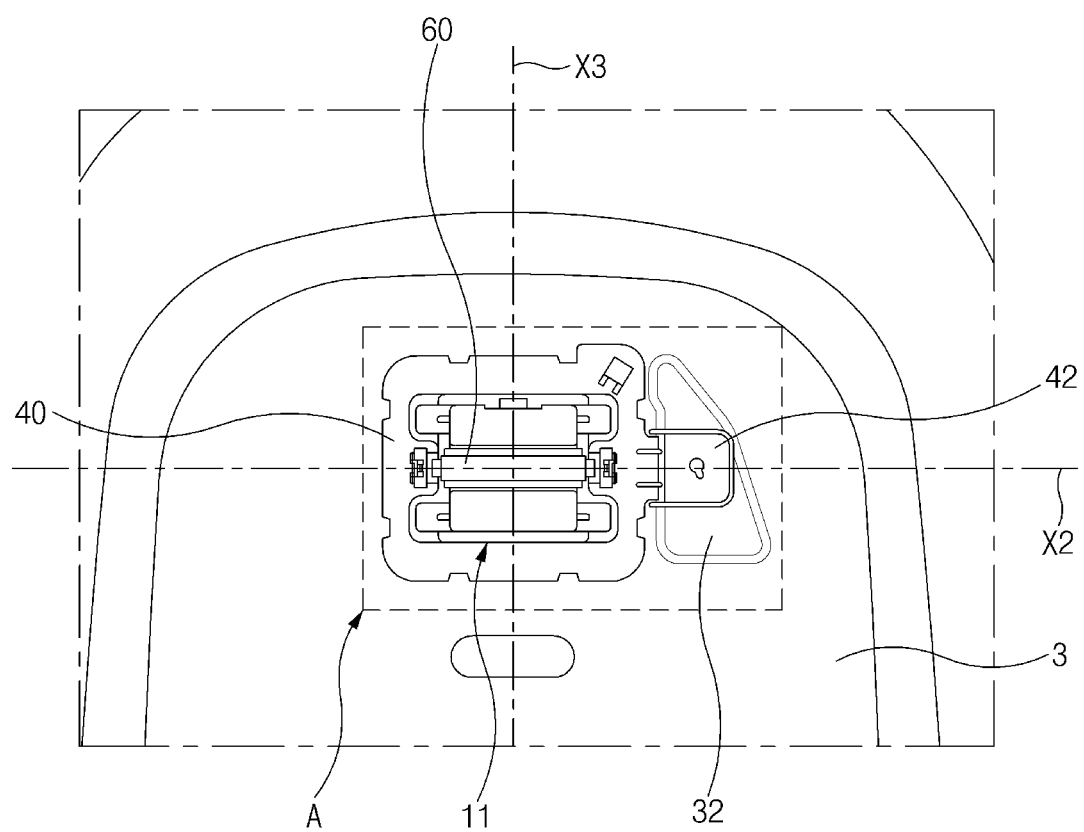
FIG. 2 illustrates a state in which a contactless sensor mounting system for a vehicle according to an exemplary embodiment of the present disclosure is mounted in a seatback foam pad.
Figure 3:
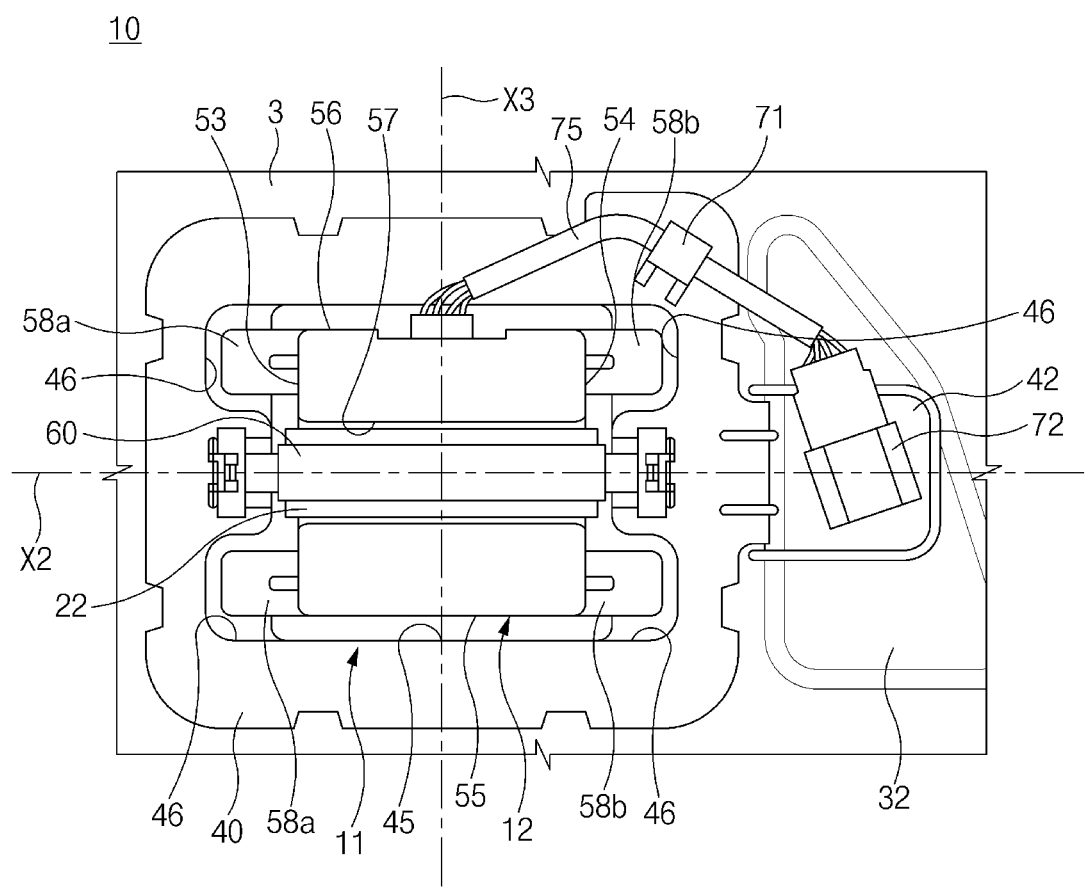
FIG. 3 illustrates a portion indicated by arrow A of FIG. 2 according to an exemplary embodiment of the present disclosure.
Figure 4:
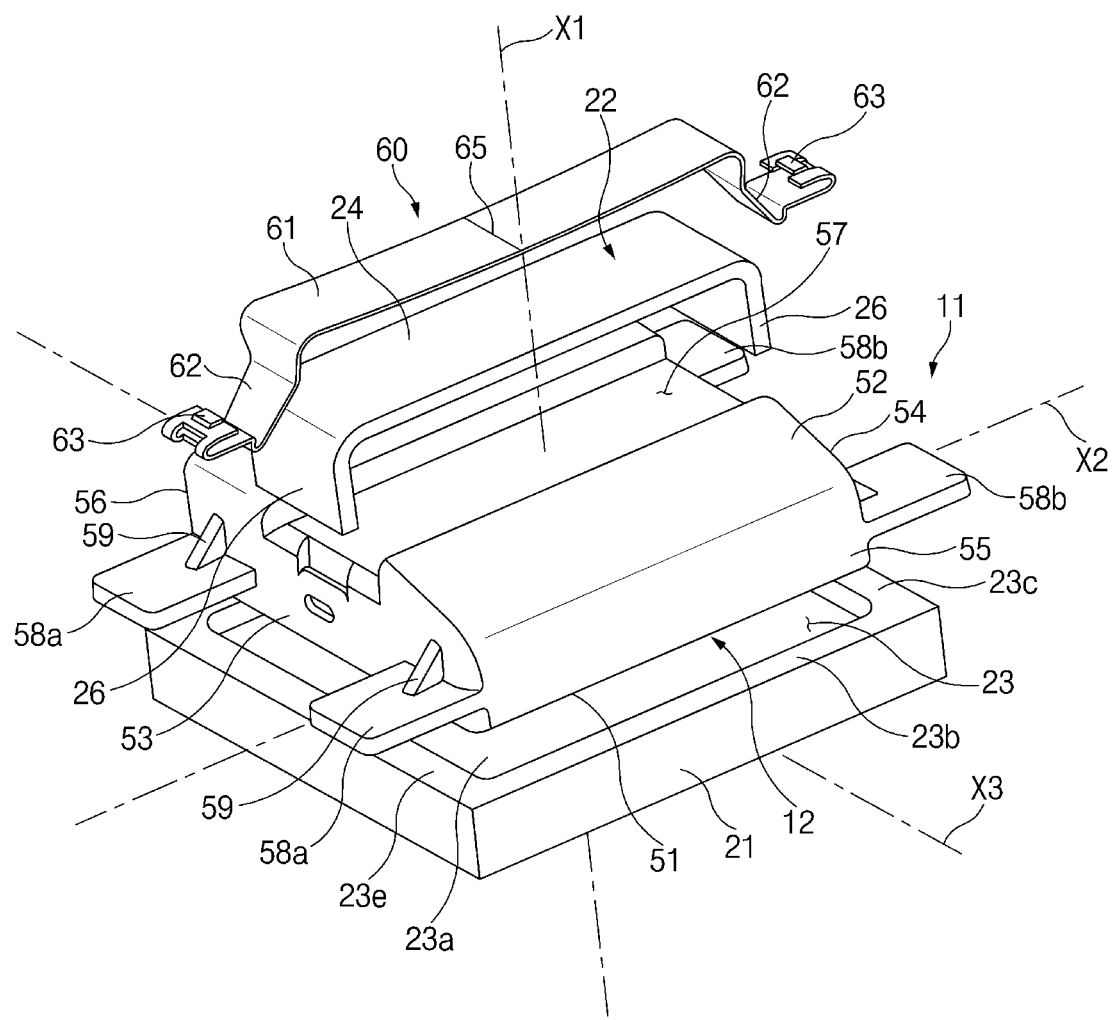
FIG. 4 illustrates a detailed perspective view of a contactless sensor mounting system for a vehicle according to an exemplary embodiment of the present disclosure.

Referring to FIGS. 2 and 3, the radar pulse sensor 11 may be mounted in the seatback foam pad 3 of the seatback 2 by a bracket 40 and a leaf spring 60. Referring to FIGS. 3 and 4, the radar pulse sensor 11 may include a sensor housing 12. The transmitter, the receiver, an evaluation circuit, and the like may be embedded in the sensor housing 12. The sensor housing 12 may have a plurality of surfaces 51, 52, 53, 54, 55, and 56. The radar pulse sensor 11 may be fixed along a first axis X1, a second axis X2, and a third axis X3 which are orthogonal to one another. The sensor housing 12 may have a first surface 51 and a second surface 52 which are orthogonal to the first axis X1, and the first surface 51 and the second surface 52 may oppose each other. The first surface 51 may face the seatback foam pad 3, and the second surface 52 may be located far from the seatback foam pad 3. The second surface 52 may include a groove 57 in which a second buffer member 22 to be described below is received. The sensor housing 12 may have a third surface 53 and a fourth surface 54 which are orthogonal to the second axis X2, and the third surface 53 and the fourth surface 54 may oppose each other. The sensor housing 12 may have a fifth surface 55 and a sixth surface 56 which are orthogonal to the third axis X3, and the fifth surface 55 and the sixth surface 56 may oppose each other.

Figure 5:
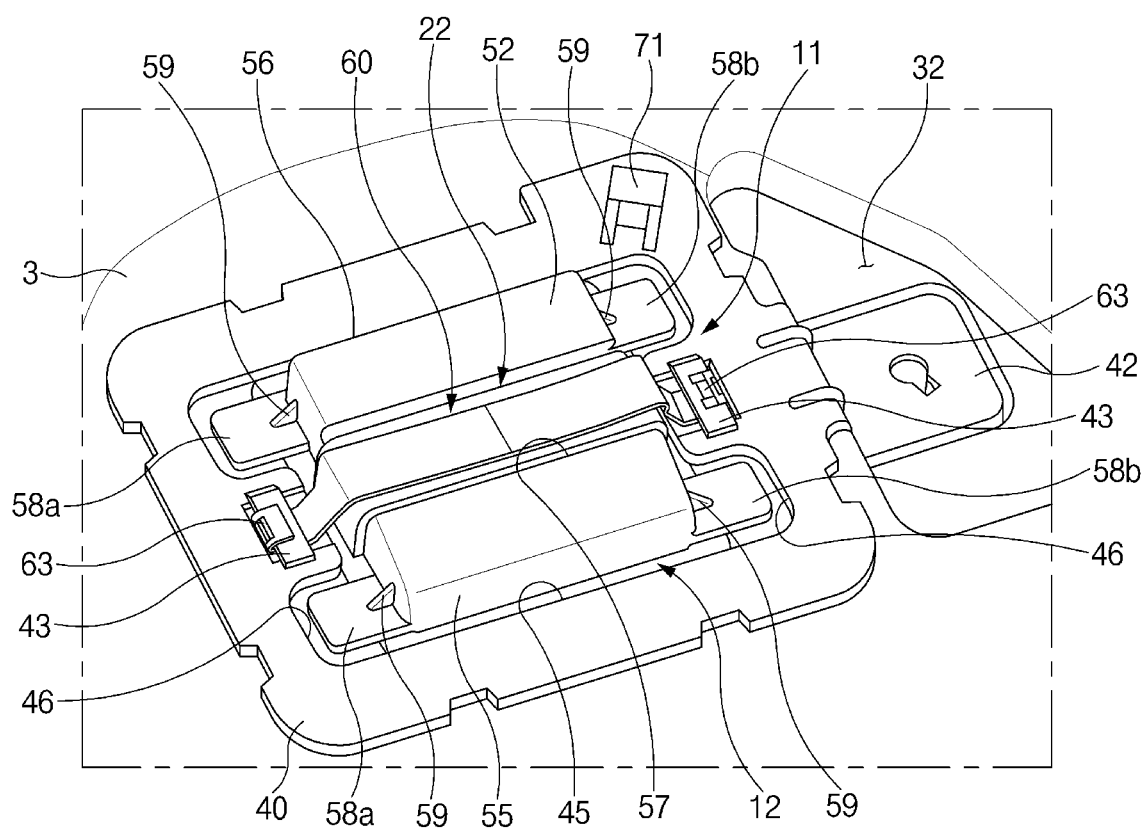
FIG. 5 illustrates a perspective view of a contactless sensor mounting system for a vehicle according to an exemplary embodiment of the present disclosure.

Referring to FIGS. 2, 3, and 5, the bracket 40 may include a mounting lug 42, and the mounting lug 42 may be coupled to the seatback foam pad 3 of the seatback 2 using fasteners (e.g., a screw, or other coupling device), and thus, the bracket 40 may be fixed to the seatback foam pad 3. The bracket 40 may be disposed around the radar pulse sensor 11. Specifically, the bracket 40 may include a main opening 45 in which the radar pulse sensor 11 is received. In particular, the main opening 45 of the bracket 40 may have a greater area than an area of the first surface 51 of the radar pulse sensor 11, and an exterior surface of the radar pulse sensor 11 may be spaced apart from an edge of the main opening 45 of the bracket 40. Thus, the bracket 40 may avoid direct contact with the radar pulse sensor 11.

In other words, the bracket 40 may surround the periphery of the radar pulse sensor 11, and the exterior surface of the radar pulse sensor 11 may be spaced apart from the edge of the main opening 45 of the bracket 40. The bracket 40 may have a plurality of side openings 46 in which support lugs 58a and 58b of the radar pulse sensor 11 are received, and each side opening 46 may extend from the main opening 45 along the second axis X2. Each side opening 46 may have a greater area than that of each of the support lugs 58a and 58b, and thus, exterior surfaces of the support lugs 58a and 58b may be spaced apart from edges of the side openings 46, respectively. Thus, the bracket 40 may avoid direct contact with the radar pulse sensor 11.

The radar pulse sensor 11 may be spaced apart from the driver by a predetermined distance. Particularly, the predetermined distance may be a minimum distance for achieving the sensing performance of the radar pulse sensor 11. According to an exemplary embodiment of the present disclosure, a first buffer member 21 having a pad shape may be interposed between the radar pulse sensor 11 and the seatback foam pad 3 so that the radar pulse sensor 11 may be spaced apart from the driver by the predetermined distance.

Figure 16:
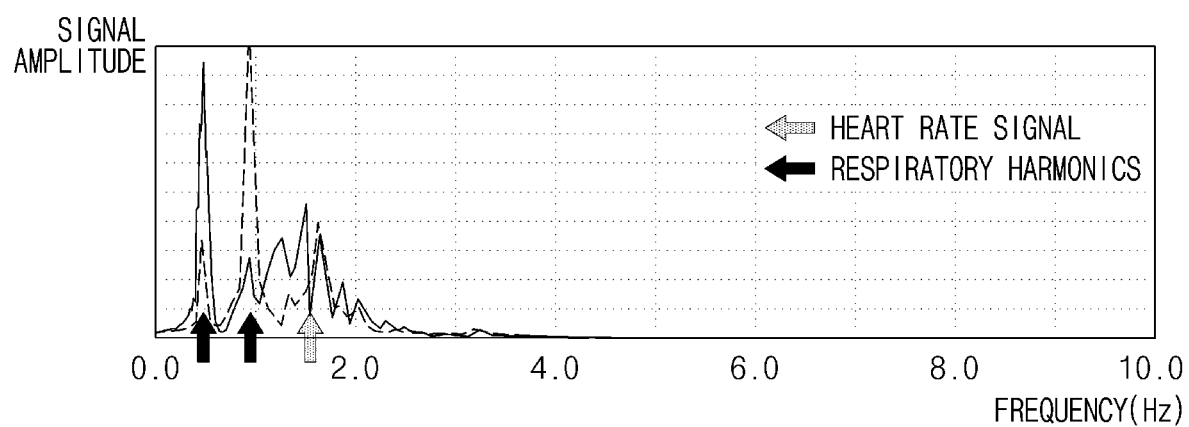
FIG. 16 illustrates a graph obtained by converting a signal output from an acceleration sensor mounted in a vehicle through FFT analysis in a condition in which a radar pulse sensor is mounted in a seatback foam pad without a first buffer member according to an exemplary embodiment of the present disclosure.

FIG. 16 illustrates a graph obtained by converting a signal output from the acceleration sensor through FFT analysis in the following conditions: the radar pulse sensor 11 is mounted in the seatback foam pad 3 without the first buffer member 21; the distance between the driver and the radar pulse sensor 11 is about 3-4 cm; and the driver's heart (pulse) rate is approximately 90-100 beats per minute (bpm). Referring to FIG. 16, since respiratory harmonics are higher than a heart rate signal in the fundamental frequency band of the heart rate, it may be difficult to analyze the heart rate signal.

Figure 17:
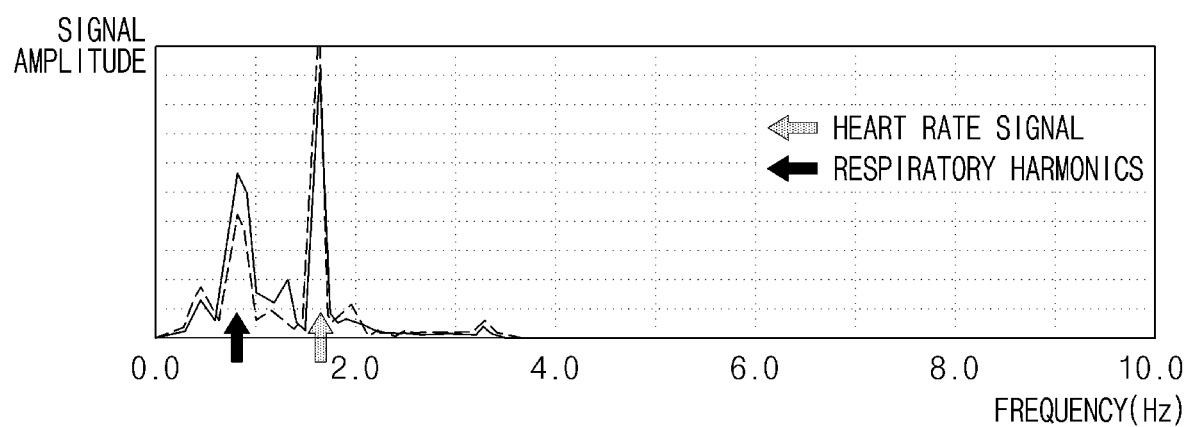
FIG. 17 illustrates a graph obtained by converting a signal output from an acceleration sensor mounted in a vehicle through FFT analysis in a condition in which a first buffer member is interposed between a radar pulse sensor and a seatback foam pad according to an exemplary embodiment of the present disclosure.

FIG. 17 illustrates a graph obtained by converting a signal output from the acceleration sensor through FFT analysis in the following conditions: the first buffer member 21 is interposed between the radar pulse sensor 11 and the seatback foam pad 3; the distance between the driver and the radar pulse sensor 11 is about 3-5 cm; and the driver's heart (pulse) rate is approximately 90-100 bpm. Referring to FIG. 17, since the respiratory harmonics are lower than the heart rate signal in the fundamental frequency band of the heart rate, it may not affect the analysis of the heart rate signal.

Figure 8:
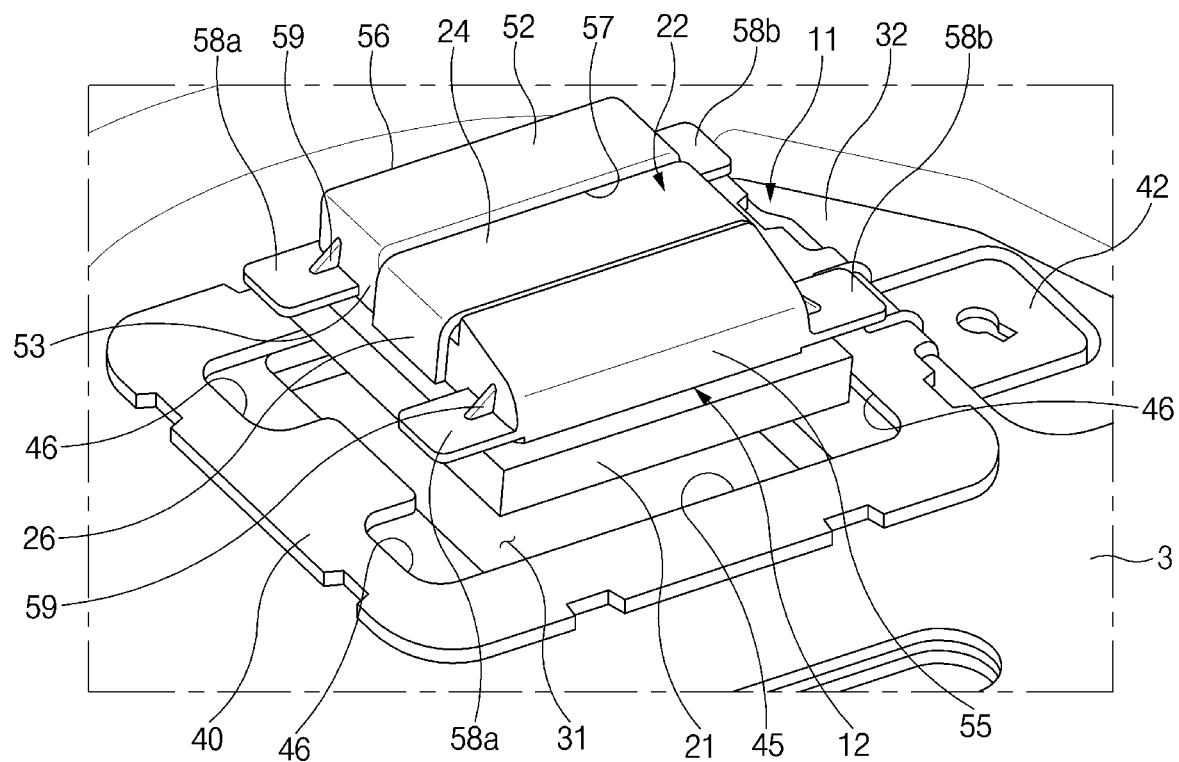
FIG. 8 illustrates a detailed perspective view of a state in which a first buffer member, a contactless sensor, a second buffer member, and a leaf spring in a contactless sensor mounting system for a vehicle according to an exemplary embodiment of the present disclosure are separated from a first recess of an interior component.
Figure 9:
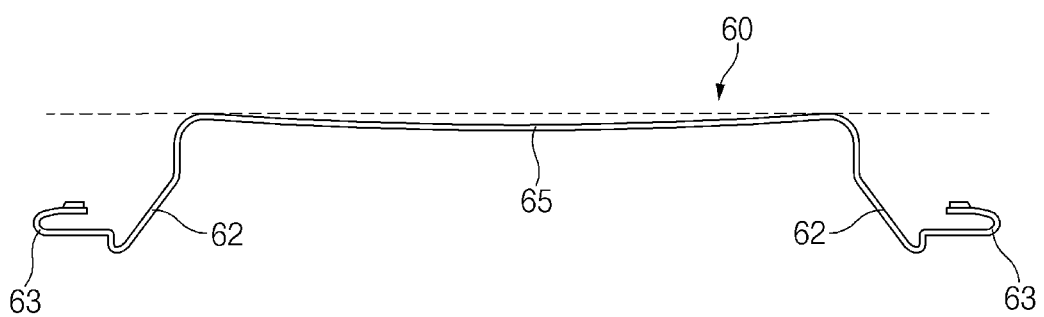
FIG. 9 illustrates a cross-sectional view of a leaf spring in a contactless sensor mounting system for a vehicle according to an exemplary embodiment of the present disclosure.

Referring to FIG. 8, the seatback foam pad 3 may have a first recess 31 in which a lower portion of the radar pulse sensor 11 is received, and a second recess 32 in which the mounting lug 42 of the bracket 40 is received. The radar pulse sensor 11 may be mounted in the first recess 31 of the seatback foam pad 3 through the first buffer member 21, and the mounting lug 42 of the bracket 40 may be mounted in the second recess 32 of the seatback foam pad 3 using fasteners and/or the like. The first buffer member 21 may be made of a resilient absorbent material capable of absorbing vibration, such as urethane and rubber. Since the first buffer member 21 absorbs or reduces the vibration or shock, the transmission of the vibration or shock to the radar pulse sensor 11 may be minimized or prevented.

Figure 7:
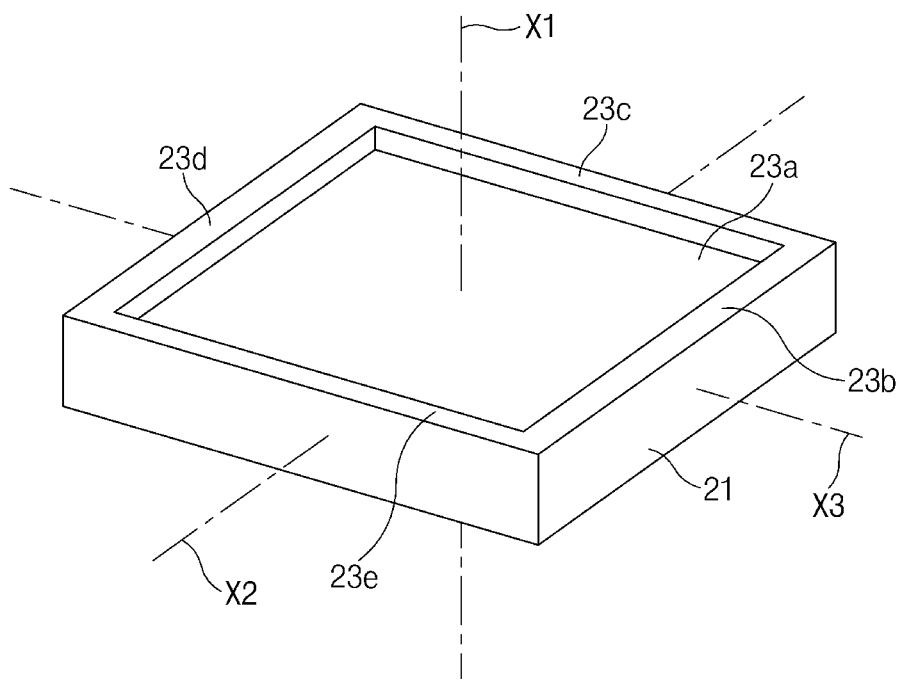
FIG. 7 illustrates a perspective view of a first buffer member in a contactless sensor mounting system for a vehicle according to an exemplary embodiment of the present disclosure.

Referring to FIG. 8, the first buffer member 21 may be received in the first recess 31 of the seatback foam pad 3. Referring to FIGS. 4 and 7, the first buffer member 21 may include a depression recess 23 in which at least a portion of the radar pulse sensor 11 is received, and the depression recess 23 may be defined by a bottom 23a and a plurality of edge walls 23b, 23c, 23d, and 23e. The bottom 23a of the first buffer member 21 may be orthogonal to the first axis X1. Two opposing edge walls 23c and 23e may be orthogonal to the second axis X2, and two opposing edge walls 23b and 23d may be orthogonal to the third axis X3, and thus the two opposing edge walls 23c and 23e may be orthogonal to the two opposing edge walls 23b and 23d.

For example, the first surface 51 of the radar pulse sensor 11 may directly contact the bottom 23a of the depression recess 23, the third surface 53 of the radar pulse sensor 11 may directly contact the edge wall 23e, the fourth surface 54 of the radar pulse sensor 11 may directly contact the edge wall 23c, the fifth surface 55 of the radar pulse sensor 11 may directly contact the edge wall 23b, and the sixth surface 56 of the radar pulse sensor 11 may directly contact the edge wall 23d. Thus, the radar pulse sensor 11 may be elastically supported by the first buffer member 21 along the first axis X1, the second axis X2, and the third axis X3. In particular, as the portion of the radar pulse sensor 11 is received in the depression recess 23 of the first buffer member 21, the radar pulse sensor 11 may not directly contact the seatback foam pad 3 and thus, the driver's respiration and the vehicle vibration may be prevented from being transmitted to the radar pulse sensor 11.

Table 1 illustrates the specification of the first buffer member 21 as an example.

TABLE 1

|  | Unit | Standard | Results | Test Method |
|---|---|---|---|---|
| Density | kg/m$^3$ | 18 ± 1 | 17.8 | KS M 6672 |
| 25% ILD | kg/314 cm$^2$ | 8 ± 2 | 8.2 | KS M 6672 |
| Ball Rebound | % | 30 or greater | 36 | KS M ISO 8307 |
| Tensile Strength | kg/cm$^2$ | 0.7 or greater | 0.93 | KS M 6579 |
| Elongation | % | 130 or greater | 158 | KS M 6579 |
| Compression Set | % | 20 or less | 9.0 | KS M 6672 |
| Tear Strength | kg/cm | 0.3 or greater | 0.35 | ASTM D 3574 |
| Burning Rate | mm/Min | 100 or less | Pass | MVSS 302 |

In particular, the first buffer member 21 may be made of a material having a lower hardness than that of the seatback foam pad 3. The second buffer member 22 may be made of a resilient absorbent material capable of absorbing vibration, such as urethane and rubber. Since the second buffer member 22 absorbs or reduces the vibration or shock, the transmission of the vibration or shock to the radar pulse sensor 11 may be minimized or prevented.

Referring to FIG. 8, the second buffer member 22 may have a base 24 attached to the second surface 52 of the radar pulse sensor 11, and a pair of legs 26 that extend from both ends of the base 24 toward the first buffer member 21. The base 24 of the second buffer member 22 may be inserted or fitted into the groove 57 of the second surface 52 of the radar pulse sensor 11, and the pair of legs 26 may be attached to the third surface 53 and the fourth surface 54 of the radar pulse sensor 11.

Since the first buffer member 21 supports a portion of the radar pulse sensor 11 including the first surface 51, and the second buffer member 22 supports a portion of the radar pulse sensor 11 including the second surface 52, the first buffer member 21 and the second buffer member 22 may sufficiently absorb or reduce the vibration or shock, thereby minimizing or preventing the transmission of the vibration or shock to the radar pulse sensor 11.

Additionally, since the radar pulse sensor 11 may be fitted into the first buffer member 21 and/or the seatback foam pad 3, the transmission of the vehicle vibration to the radar pulse sensor 11 may be minimized. According to an exemplary embodiment of the present disclosure, the leaf spring 60 may press or push the second buffer member 22 and the radar pulse sensor 11 toward the seatback foam pad 3 and thus, the radar pulse sensor 11 may be fitted into the first buffer member 21 and/or the seatback foam pad 3.

Figure 18:
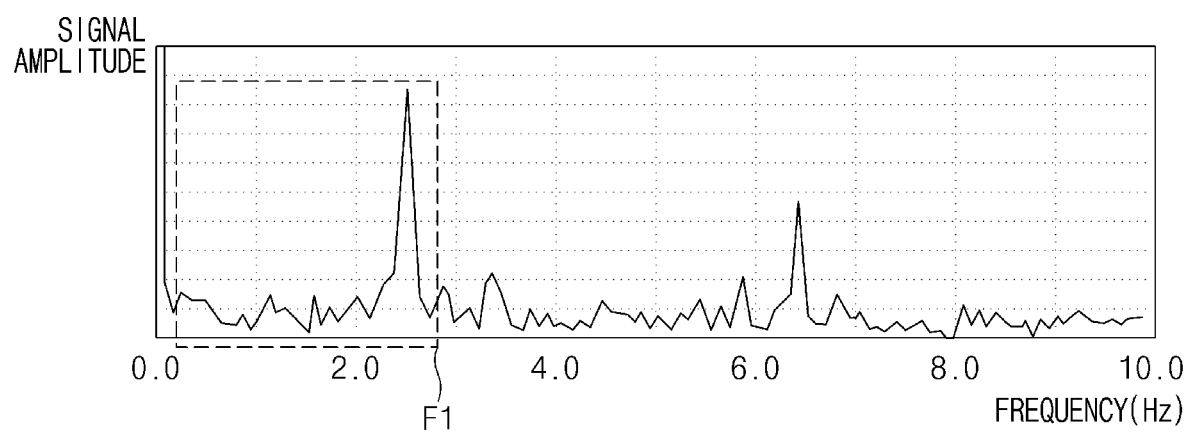
FIG. 18 illustrates a graph obtained by converting a signal output from an acceleration sensor mounted in a vehicle through FFT analysis in a condition in which a radar pulse sensor is mounted in a seatback foam pad without a leaf spring according to an exemplary embodiment of the present disclosure.

FIG. 18 illustrates a graph obtained by converting a signal output from the acceleration sensor through FFT analysis in the following conditions: the radar pulse sensor 11 is mounted in the seatback foam pad 3 without the leaf spring 60; the distance between the driver and the radar pulse sensor 11 is about 3-4 cm; and the vehicle is accelerating. Referring to FIG. 18, noise due to respiration is detected in the fundamental frequency band F1 of the heart rate.

Figure 19:
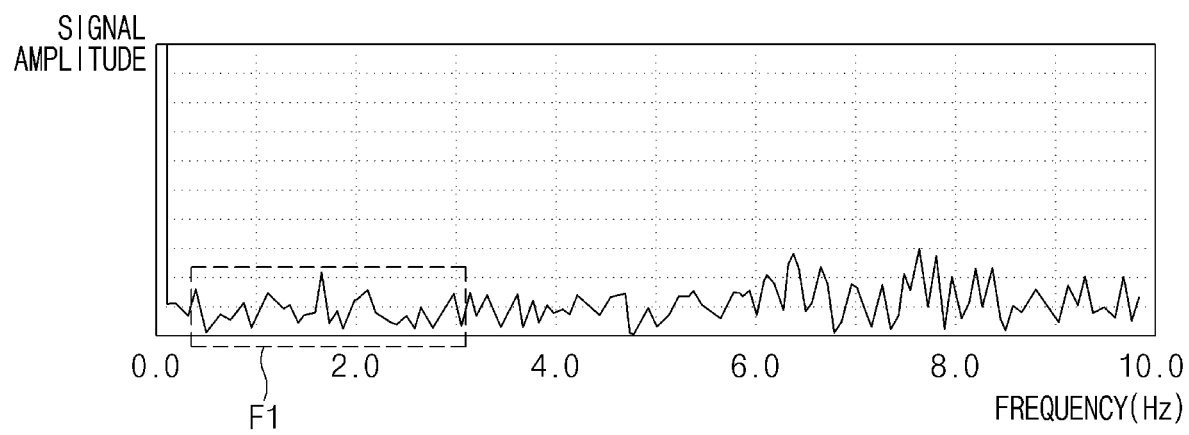
FIG. 19 illustrates a graph obtained by converting a signal output from an acceleration sensor mounted in a vehicle through FFT analysis in a condition in which a radar pulse sensor is pressed to a seatback foam pad by a leaf spring according to an exemplary embodiment of the present disclosure.

FIG. 19 illustrates a graph obtained by converting a signal output from the acceleration sensor through FFT analysis in the following conditions: the radar pulse sensor 11 is pressed to the seatback foam pad 3 by the leaf spring 60; the distance between the driver and the radar pulse sensor 11 is about 3-5 cm; and the vehicle is accelerating. Referring to FIG. 19, noise due to respiration is hardly detected in the fundamental frequency band F1 of the heart rate.

The leaf spring 60 may be disposed on the second buffer member 22, and the second buffer member 22 may be interposed between the leaf spring 60 and the radar pulse sensor 11. The leaf spring 60 may include a spring portion 61 elastically pressing the base 24 of the second buffer member 22, and a pair of resilient legs 62 that extend from both ends of the spring portion 61 toward the bracket 40. The spring portion 61 may be convexly curved toward the second buffer member 22, and thus, a central portion 65 of the spring portion 61 may protrude toward the second buffer member 22 compared to both ends of the spring portion 61. Each resilient leg 62 may extend from the end of the spring portion 61 to be inclined toward the bracket 40.

The leaf spring 60 may have a pair of first snap fitting portions 63, and the first snap fitting portions 63 may be formed at the ends of the resilient legs 62, respectively. The bracket 40 may have a pair of second snap fitting portions 43 that correspond to the pair of first snap fitting portions 63 of the leaf spring 60. Since the first snap fitting portions 63 of the leaf spring 60 are snap-fitted to the second snap fitting portions 43 of the bracket 40, respectively, the leaf spring 60 may elastically press the second buffer member 22 and the radar pulse sensor 11 toward the first buffer member 21.

Further, since the second buffer member 22 may be interposed between the leaf spring 60 and the radar pulse sensor 11, the leaf spring 60 may be prevented from directly contacting the radar pulse sensor 11. Since direct friction between the leaf spring 60 made of a metal material and the radar pulse sensor 11 is prevented, friction noise may not be generated. In addition, since the second buffer member 22 may be interposed between the leaf spring 60 and the radar pulse sensor 11, minute movements of the radar pulse sensor 11 due to assembly tolerance of the leaf spring 60 may be minimized.

The radar pulse sensor 11 may be firmly fixed to the seatback foam pad 3 through the leaf spring 60 and the bracket 40, and the leaf spring 60 may press the second buffer member 22 and the radar pulse sensor 11 toward the first buffer member 21 and thus, the first surface 51 of the radar pulse sensor 11 may be elastically supported by the first buffer member 21, and the second surface 52 of the radar pulse sensor 11 may be elastically supported by the second buffer member 22. Thus, the transmission of the vibration to the radar pulse sensor 11 may be minimized.

Figure 10:
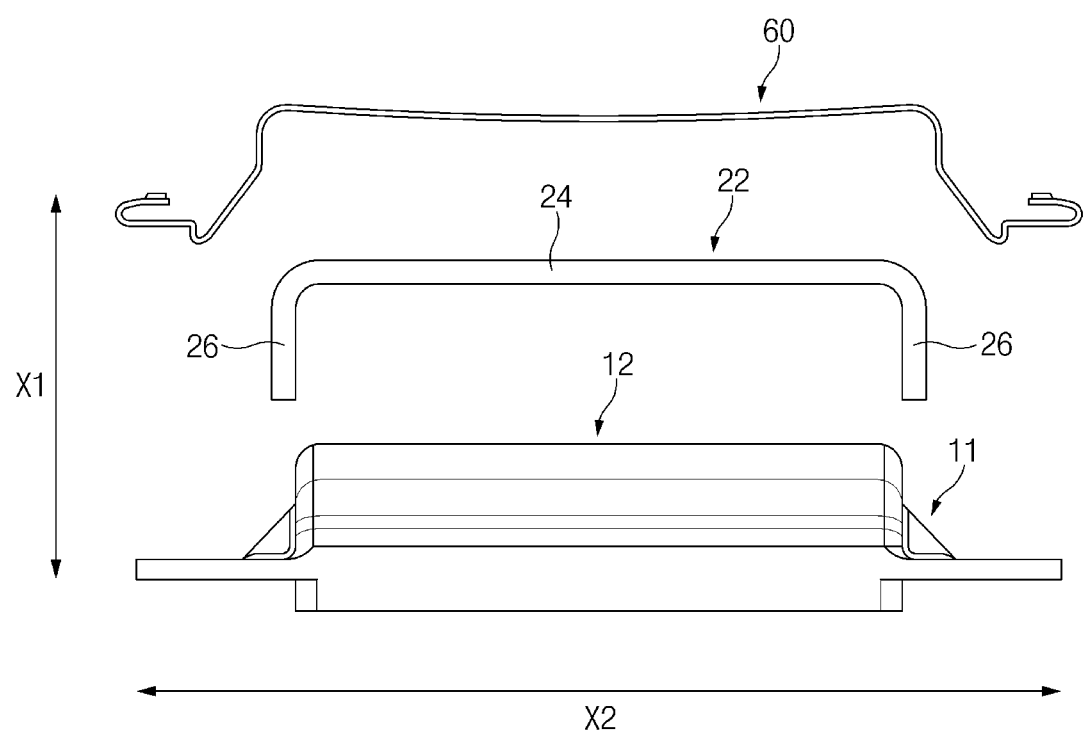
FIG. 10 illustrates a detailed perspective view of a leaf spring, a second buffer member, and a contactless sensor in a contactless sensor mounting system for a vehicle according to an exemplary embodiment of the present disclosure.
Figure 11:
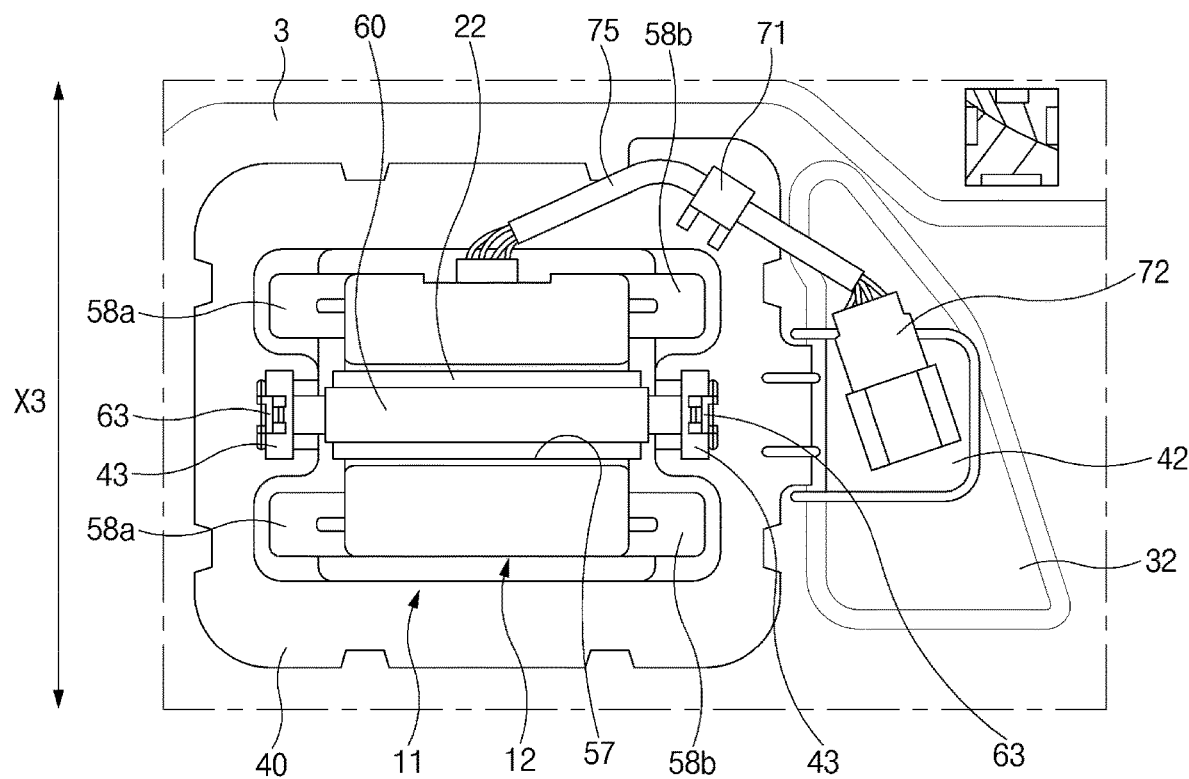
FIG. 11 illustrates a contactless sensor mounting system for a vehicle according to an exemplary embodiment of the present disclosure.

Referring to FIG. 10, the radar pulse sensor 11 may be fixed by the leaf spring 60 along the first axis X1, and be fixed by the second buffer member 22 along the second axis X2. Referring to FIG. 11, a width of the leaf spring 60 may be less than a width of the second buffer member 22, and the leaf spring 60 may be positioned in the width-direction middle of the second buffer member 22. The leaf spring 60 and the second buffer member 22 may stably fix the radar pulse sensor 11, thereby effectively preventing the radar pulse sensor 11 from slightly moving along the third axis X3.

Figure 6:
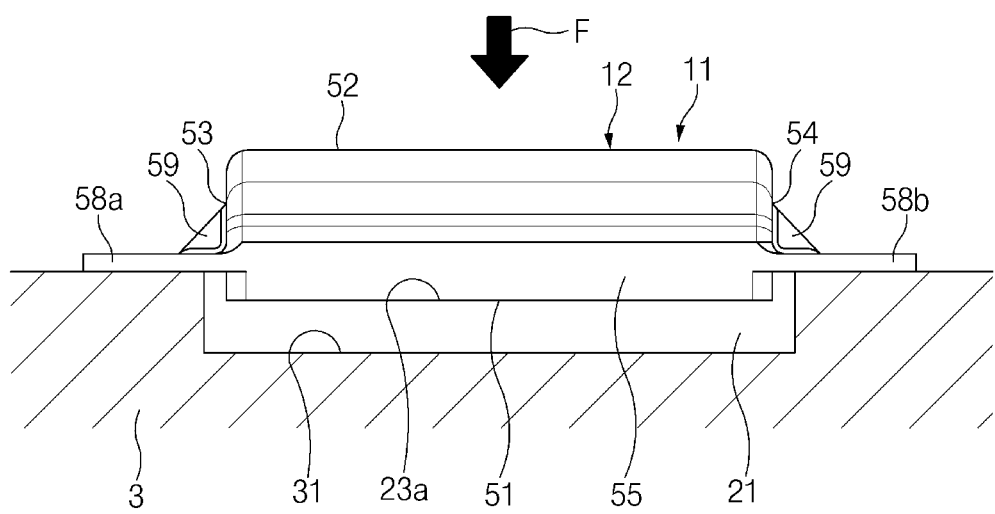
FIG. 6 illustrates a state of a contactless sensor mounting system for a vehicle according to an exemplary embodiment of the present disclosure, in which a contactless sensor is mounted in a first recess of an interior component through a first buffer member, and a leaf spring and a second buffer member are removed.

Referring to FIGS. 5 and 6, the radar pulse sensor 11 may include the plurality of support lugs 58*a* and 58*b*. Two first support lugs 58*a* may extend from the third surface 53 of the sensor housing 12, and two second support lugs 58*b* may extend from the fourth surface 54 of the sensor housing 12. Since the plurality of support lugs 58*a* and 58*b* are supported by portions of the seatback foam pad 3 adjacent to the periphery of the first recess 31, the radar pulse sensor 11 may be prevented from being excessively pressed into the first recess 31 of the seatback foam pad 3 by a spring force F of the leaf spring 60.

Referring to FIG. 11, an electric wire 75 may extend from the radar pulse sensor 11, and an electrical connector 72 may be connected to an end of the electric wire 75. A holding member 71 for holding the electric wire 75 may be fixed to a top surface of the bracket 40, and the holding member 71 may be a clamp, a clip, or the like. Since the holding member 71 that holds the electric wire 75 is coupled to the bracket 40, the movement of the electric wire 75 may be minimized.

The electrical connector 72 may be coupled to a top surface of the mounting lug 42 using fasteners and/or the like. Since the electrical connector 72 is coupled to the top surface of the mounting lug 42, the movement of the electrical connector 72 may be minimized or prevented. In particular, as the electrical connector 72 is coupled to the top surface of the mounting lug 42, the electrical connector 72 may be received in the second recess 32 of the seatback foam pad 3, and thus, the electrical connector 72 may be prevented from interfering or colliding with a seatback cover or the like of the seatback 2.

As set forth above, the contactless sensor mounting system, according to exemplary embodiments of the present disclosure, may minimize the vibration transmitted to the contactless sensor mounted in the interior component of the vehicle such as the seat, thereby improving the sensing performance of the contactless sensor, and minimizing the exposure of the contactless sensor.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

What is claimed is:

1. A contactless sensor mounting system for a vehicle, comprising:
   a contactless sensor mounted within an interior component of the vehicle, and having a first surface and a second surface opposing each other;
   a bracket disposed around the contactless sensor, and fixed to the interior component;
   a first buffer member interposed between the first surface of the contactless sensor and the interior component;

a second buffer member mounted on the second surface of the contactless sensor; and a leaf spring pressing the second buffer member and the contactless sensor toward the interior component, wherein the bracket has a mounting lug which is coupled to the interior component.

2. The contactless sensor mounting system according to claim 1, wherein the bracket includes a main opening in which the contactless sensor is received, and an exterior surface of the contactless sensor is spaced apart from an edge of the main opening.

3. The contactless sensor mounting system according to claim 1, wherein the interior component has a first recess in which the first buffer member is received, and a second recess in which the mounting lug is received.

4. The contactless sensor mounting system according to claim 3, wherein the first buffer member has a depression recess in which at least a portion of the contactless sensor is received.

5. The contactless sensor mounting system according to claim 1, wherein the second buffer member includes a base attached to the second surface of the contactless sensor, and a pair of legs that extend from both ends of the base toward the first buffer member, respectively.

6. The contactless sensor mounting system according to claim 5, wherein the leaf spring includes a spring portion that supports the base, and a pair of resilient legs that extend from both ends of the spring portion toward the bracket.

7. The contactless sensor mounting system according to claim 6, wherein the leaf spring has a pair of first snap fitting portions, the first snap fitting portions are formed at ends of the resilient legs, respectively, and wherein the bracket includes a pair of second snap fitting portions, and the first snap fitting portions are snap-fitted to the second snap fitting portions, respectively.

8. The contactless sensor mounting system according to claim 3, wherein the contactless sensor includes a plurality of support lugs supported by portions of the interior component adjacent to a periphery of the first recess.

9. The contactless sensor mounting system according to claim 1, wherein a holding member for holding an electric wire extending from the contactless sensor is fixed to a top surface of the bracket.

10. The contactless sensor mounting system according to claim 1, wherein an electrical connector is fixed to a top surface of the mounting lug.

* * * * *